(12) United States Patent
Neethling et al.

(10) Patent No.: US 11,648,107 B2
(45) Date of Patent: May 16, 2023

(54) REPLACEMENT HEART VALVE WITH REDUCED SUTURING

(71) Applicant: Anteris Technologies Corporation, Eagan, MN (US)

(72) Inventors: William Morris Leonard Neethling, Booragoon (AU); Scott Bliss, Minneapolis, MN (US); Anthony Michael MacIntyre, Claremont (AU); Wayne Paterson, Mendota Heights, MN (US)

(73) Assignee: Anteris Technologies Corporation, Eagan, MN (US)

( * ) Notice: Subject to any disclaimer, the term of this patent is extended or adjusted under 35 U.S.C. 154(b) by 0 days.

(21) Appl. No.: 16/129,235

(22) Filed: Sep. 12, 2018

(65) Prior Publication Data

US 2019/0117390 A1 Apr. 25, 2019

Related U.S. Application Data

(60) Provisional application No. 62/574,410, filed on Oct. 19, 2017.

(51) Int. Cl.
*A61F 2/24* (2006.01)
*A61F 2/86* (2013.01)

(52) U.S. Cl.
CPC .......... *A61F 2/2418* (2013.01); *A61F 2/2412* (2013.01); *A61F 2/2433* (2013.01);
(Continued)

(58) Field of Classification Search
CPC ............ A61F 2/2412; A61F 2250/0036; A61F 2310/00371; A61F 2/2418;
(Continued)

(56) References Cited

U.S. PATENT DOCUMENTS 4,624,822 A * 11/1986 Arru ..................... A61F 2/2415
623/901
5,855,601 A * 1/1999 Bessler ................. A61F 2/2418
623/2.38
(Continued)

FOREIGN PATENT DOCUMENTS

CN 203736349 7/2014
EP 2777618 A1 9/2014
(Continued)

OTHER PUBLICATIONS

Knee Hiang Lim et al., "Flat or Curved Pericardial Aortic Valve Cusps: A Finite Element Study", The Journal of Heart Valve Disease Sep. 2004; vol. 13, No. 5, pp. 792-797.
(Continued)

*Primary Examiner* — Brian E Pellegrino

(57) ABSTRACT

A heart valve replacement device comprises a stent having a first end, a second end, an outer surface, and an inner surface, the inner surface defining a lumen; and a valve disposed within the lumen of the stent, the valve formed from a single sheet of tissue, the valve having an outer surface, an inner surface, and a thickness between the outer surface and the inner surface, the valve comprising at least three leaflets, wherein, the valve is attached to the stent with minimal sutures. The leaflets are formed with a curvilinear surface.

8 Claims, 15 Drawing Sheets

(52) U.S. Cl.
CPC .......... *A61F 2/2442* (2013.01); *A61F 2/2415* (2013.01); *A61F 2/86* (2013.01); *A61F 2220/0075* (2013.01); *A61F 2250/0036* (2013.01)

(58) Field of Classification Search
CPC ........ A61F 2220/0075; A61F 2220/005; A61F 2250/0003; A61F 2/2415; A61L 31/044
USPC ....................................................... 623/2.13
See application file for complete search history.

(56) References Cited

U.S. PATENT DOCUMENTS

| | | | |
|---|---|---|---|
| 6,491,511 B1 | 12/2002 | Duran et al. | |
| 6,682,559 B2* | 1/2004 | Myers | A61F 2/2412 623/2.13 |
| 7,025,780 B2* | 4/2006 | Gabbay | A61F 2/2418 623/2.13 |
| 7,087,079 B2 | 8/2006 | Navia et al. | |
| 8,778,018 B2 | 7/2014 | Iobbi | |
| 8,992,599 B2 | 3/2015 | Thubrikar et al. | |
| 9,011,525 B2 | 4/2015 | Claiborne, III et al. | |
| 9,095,430 B2 | 8/2015 | Cunanan et al. | |
| 9,192,470 B2* | 11/2015 | Cai | A61F 2/2418 |
| 9,205,172 B2 | 12/2015 | Leonard Neethling et al. | |
| 9,259,313 B2 | 2/2016 | Wheatley | |
| 9,301,835 B2 | 4/2016 | Campbell et al. | |
| 9,554,902 B2 | 1/2017 | Braido et al. | |
| 9,744,037 B2 | 8/2017 | Kheradvar et al. | |
| 9,763,780 B2 | 9/2017 | Morriss et al. | |
| 11,135,059 B2 | 10/2021 | Hammer et al. | |
| 11,464,635 B2 | 10/2022 | Reimer et al. | |
| 2003/0069635 A1* | 4/2003 | Cartledge | A61F 2/2412 623/2.13 |
| 2005/0123582 A1* | 6/2005 | Sung | A61L 31/042 424/426 |
| 2005/0137687 A1 | 6/2005 | Salahieh et al. | |
| 2005/0203614 A1 | 9/2005 | Forster et al. | |
| 2005/0240262 A1* | 10/2005 | White | A61F 2/2415 623/2.12 |
| 2006/0020327 A1* | 1/2006 | Lashinski | A61F 2/2418 623/1.25 |
| 2008/0288055 A1 | 11/2008 | Paul, Jr. | |
| 2010/0049313 A1 | 2/2010 | Mon et al. | |
| 2011/0066224 A1* | 3/2011 | White | A61F 2/2418 623/1.24 |
| 2011/0238167 A1 | 9/2011 | Dove et al. | |
| 2012/0078356 A1 | 3/2012 | Fish et al. | |
| 2012/0277855 A1 | 11/2012 | Lashinski et al. | |
| 2013/0018458 A1 | 1/2013 | Yohanan et al. | |
| 2013/0184811 A1 | 7/2013 | Rowe et al. | |
| 2013/0197631 A1 | 8/2013 | Bruchman et al. | |
| 2013/0204360 A1 | 8/2013 | Gainor | |
| 2013/0310927 A1* | 11/2013 | Quintessenza | A61F 2/2412 623/2.12 |
| 2014/0005772 A1* | 1/2014 | Edelman | A61F 2/2412 623/2.17 |
| 2014/0031924 A1 | 1/2014 | Bruchman et al. | |
| 2014/0107772 A1 | 4/2014 | Li et al. | |
| 2014/0277417 A1* | 9/2014 | Schraut | A61F 2/2403 623/2.17 |
| 2014/0324160 A1 | 10/2014 | Benichou et al. | |
| 2015/0134056 A1 | 5/2015 | Claiborne, III et al. | |
| 2015/0142104 A1 | 5/2015 | Braido | |
| 2015/0209141 A1 | 7/2015 | Braido et al. | |
| 2015/0216663 A1 | 8/2015 | Braido et al. | |
| 2015/0289973 A1 | 10/2015 | Braido et al. | |
| 2015/0320556 A1 | 11/2015 | Levi et al. | |
| 2016/0128831 A1 | 5/2016 | Zhou et al. | |
| 2016/0135951 A1 | 5/2016 | Salahieh et al. | |
| 2016/0143732 A1 | 5/2016 | Glimsdale | |
| 2016/0158007 A1 | 6/2016 | Centola et al. | |
| 2016/0175095 A1 | 6/2016 | Dienno et al. | |
| 2016/0220365 A1 | 8/2016 | Backus et al. | |
| 2016/0317293 A1 | 11/2016 | Matheny et al. | |
| 2016/0331532 A1 | 11/2016 | Quadri | |
| 2016/0367360 A1 | 12/2016 | Cartledge et al. | |
| 2016/0367364 A1 | 12/2016 | Forrianni et al. | |
| 2017/0049566 A1 | 2/2017 | Zeng et al. | |
| 2017/0056170 A1 | 3/2017 | Zhu et al. | |
| 2017/0119525 A1 | 5/2017 | Rowe et al. | |
| 2017/0189174 A1 | 7/2017 | Braido et al. | |
| 2017/0258585 A1 | 9/2017 | Marquez et al. | |
| 2017/0312075 A1 | 11/2017 | Fahim et al. | |
| 2018/0028312 A1 | 2/2018 | Thill et al. | |
| 2018/0228603 A1 | 8/2018 | Racchini et al. | |
| 2020/0188099 A1 | 6/2020 | Dvorsky et al. | |
| 2021/0212819 A1 | 7/2021 | Reed et al. | |
| 2021/0212822 A1 | 7/2021 | Reed et al. | |
| 2021/0212823 A1 | 7/2021 | Reed et al. | |

FOREIGN PATENT DOCUMENTS

| | | |
|---|---|---|
| EP | 2967869 | 1/2016 |
| EP | 3697343 | 8/2020 |
| JP | 2008-264553 | 11/2008 |
| JP | 2015519187 A | 7/2015 |
| WO | 2001076510 | 10/2001 |
| WO | 2003/030776 | 4/2003 |
| WO | 2015126712 | 8/2005 |
| WO | 2007013999 | 2/2007 |
| WO | 2011072084 A2 | 6/2011 |
| WO | 2011109450 | 9/2011 |
| WO | 2014204807 A1 | 12/2014 |
| WO | 2015173794 | 11/2015 |
| WO | 2017031155 A1 | 2/2017 |
| WO | 2019144036 | 7/2019 |

OTHER PUBLICATIONS

Search Report and Written Opinion for related PCT Application No. PCT/US2018/050669 dated Nov. 26, 2018 (12 pages).

* cited by examiner

REPLACEMENT HEART VALVE WITH REDUCED SUTURING

FIELD OF THE INVENTION

The present disclosure relates to novel and advantageous heart valves formed from a biomaterial.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Native heart valves may need to be replaced when a patient has a condition such as congenital heart defect or valvular heart disease. A diseased heart valve may result in regurgitation, where the valve is not properly function and blood flows in a direction opposite the normal direction of the flow, and/or stenosis, where the valve has narrowed through in some instances calcification of the valve, some obstruction of the valve such as plaque, or inflammation. Heart valves may be replaced through surgical repair or a valve deployed relative to the native heart valve through a transcatheter approach. Transcatheter valve replacement devices generally comprise leaflets of tissue that are attached to an expandable or self-expanding stent construct that is crimped onto a catheter for deployment. The stent is advanced to the location of the troubled heart valve, where it expands or is expanded by a balloon or other means. Once seated in the valve, blood flow and the muscles of the heart will result in the tissue leaflets to open and close. When manufacturing these transcatheter valve replacement devices, one of the most time-consuming and labor-intensive portions of the process is attaching the leaflets securely to the stent. The leaflets are attached to the stent with hundreds of sutures, generally hand sewn by a skilled laborer. Often each valve replacement devices may have anywhere from 150 sutures to 300 sutures or more. To reduce the cost and time needed to manufacture these devices, it would be desirable to significantly reduce the number of sutures needed to securely attach the tissue to an expandable or self-expanding stent.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

In some embodiments, a heart valve replacement device of the present disclosure comprises a stent having a first end, a second end, an outer surface, and an inner surface, the inner surface defining a lumen; and a valve disposed within the lumen of the stent, the valve formed from a single sheet of tissue, the valve having an outer surface, an inner surface, and a thickness between the outer surface and the inner surface, the valve comprising at least three leaflets, wherein, the valve is attached to the stent with fewer than forty sutures. In some embodiments, the valve is attached to the stent with fewer than thirty sutures. In some embodiments, the valve is attached to the stent with fewer than twenty sutures. In some embodiments, the valve is attached to the stent with between three sutures and twenty sutures. In some embodiments of the present disclosure, the valve has a body portion connected to the leaflets. In at least one embodiment, the thickness of the body portion is different than the thickness of the leaflets. In some embodiments, the valve has a cuff portion, which may be connected to a body portion of the valve. In at least one embodiment, the thickness of the cuff portion is different than the thickness of the body portion. In at least one embodiment, the thickness of the cuff portion is different than the thickness of the leaflets. In at least one embodiment, the cuff portion that is expandable from a first position to a second position relative to the stent. The stent of the heart valve replacement device may have at least one attachment feature. In some embodiments, at least one suture connects the stent to the valve at the one attachment feature.

In some embodiments of the present disclosure, a replacement heart valve comprises a plurality of leaflets; and a body portion connected to the leaflets, wherein the body portion and the leaflets are formed from a single sheet of a tissue material. The replacement heart valve may comprise a cuff portion connected to the body portion. In some embodiments, the thickness of the leaflets may be different than the thickness of the cuff portion. In some embodiments, the thickness of the body portion may be different than the thickness of the cuff portion. In some embodiments, the tissue material is a biomaterial. In some embodiment, the valve comprises attachment points on at least the body portion of the heart valve.

In some embodiments, a method of manufacturing a replacement heart valve device, comprises forming a valve from a single sheet of tissue material, the valve having a body portion with at least three leaflets connected to the body portion; inserting the valve formed from a single sheet of material into a lumen of a stent; and securing the valve to the stent with fewer than forty sutures. In some embodiments, the valve is secured to the stent with fewer than thirty sutures. In some embodiments, the valve is secured to the stent with fewer than twenty sutures. In some embodiments, the valve is secured to the stent with between three and twenty sutures. In some embodiments, the step of forming the valve comprises inserting the single sheet of tissue material into a mold. The mold may have a lower portion (primary mold) and an upper portion (secondary mold). In some embodiments, the mold has a locking member for locking the upper position relative to the lower portion. In some embodiments, a spacer is inserted between the single sheet of tissue material and at least one of the upper portion and the lower portion. In some embodiments, a cross-linking process is applied to the single sheet of tissue material while in the mold. The tissue material may be an artificial tissue in some embodiments or a bio-material. In some embodiments, the single sheet of tissue material has varying thickness from one end of the material to the other. In some embodiments, the single sheet of material was cut from one end of the material to the other with a cutting device to vary the thickness from one end of the material to the other.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

Figure 1:
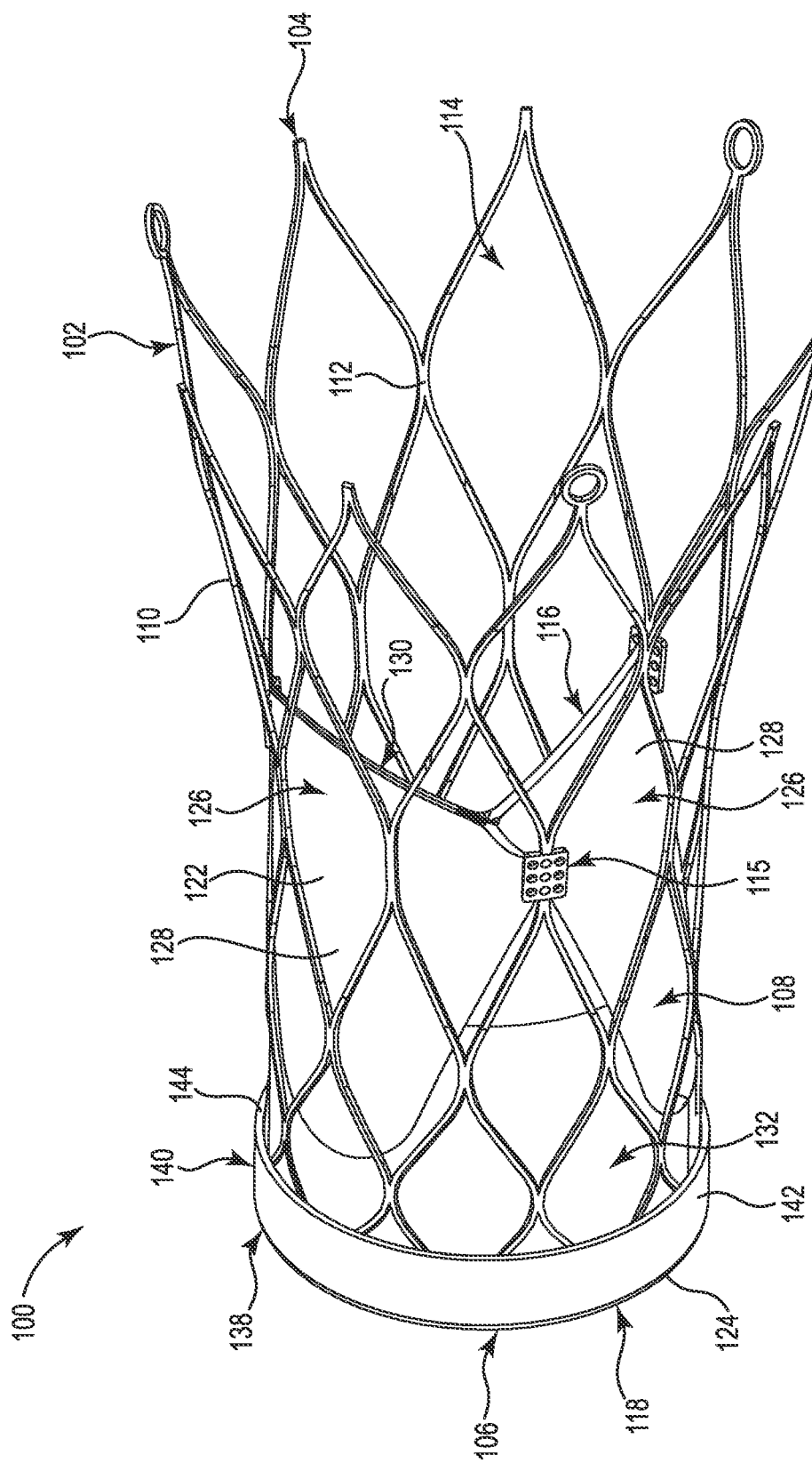
FIG. 1 is a perspective view of a heart valve replacement device comprising a heart valve disposed relative to a stent construct, in accordance with one embodiment of the present disclosure.
Figure 2:
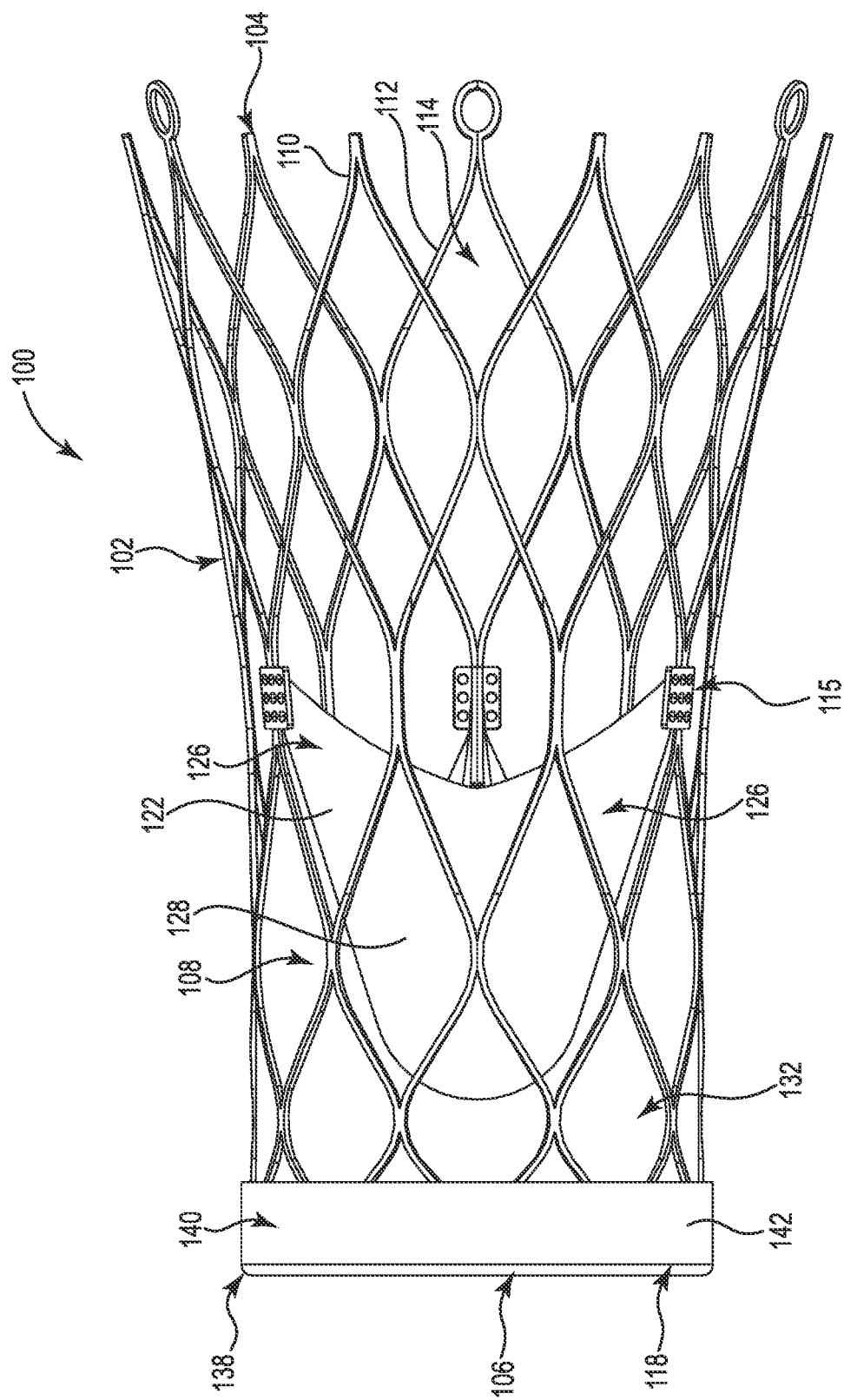
FIG. 2 is a first side view of the heart valve replacement device of FIG. 1.
Figure 3:
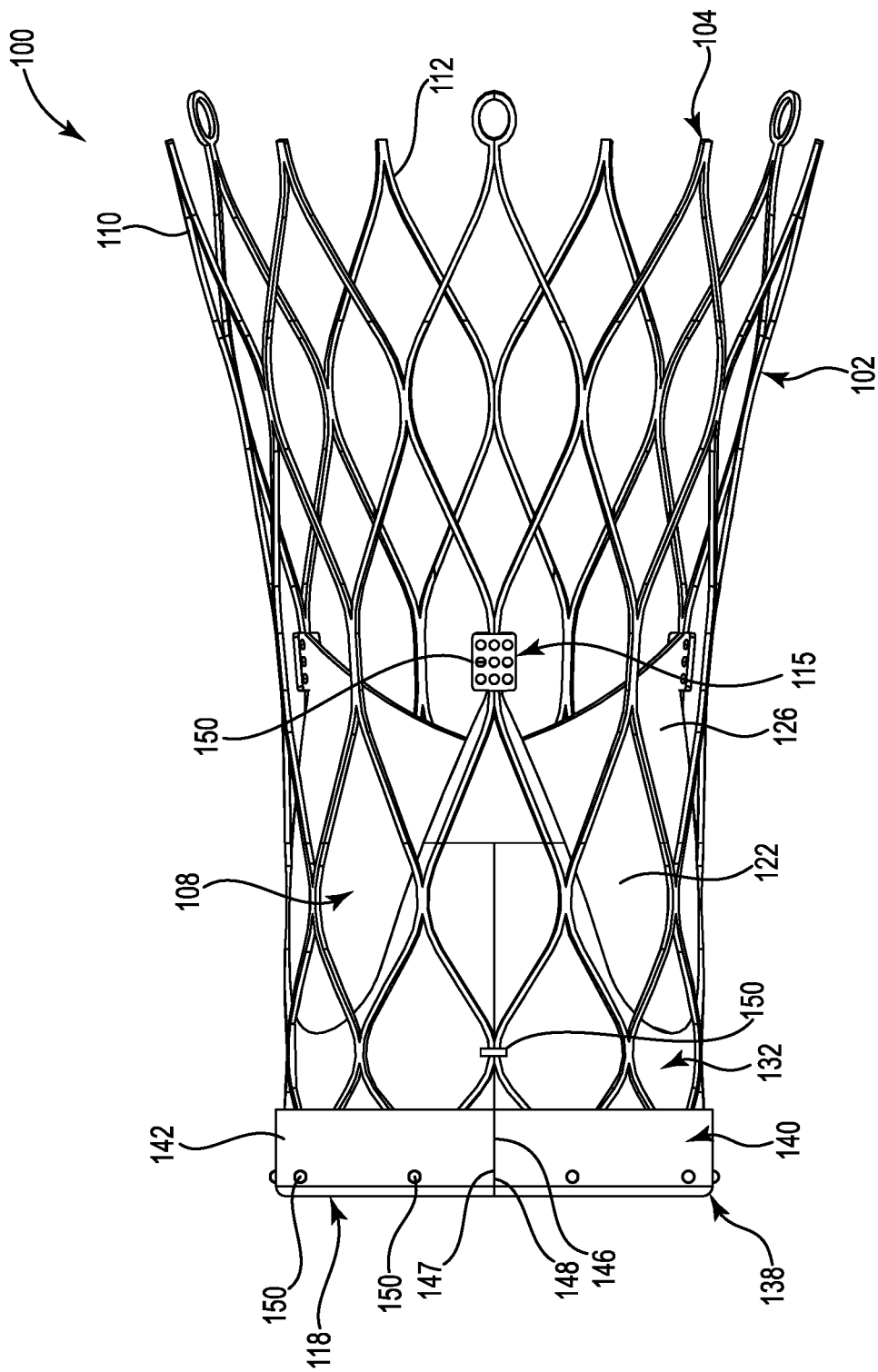
FIG. 3 is a second side view of the heart valve replacement device of FIG. 1.
Figure 4:
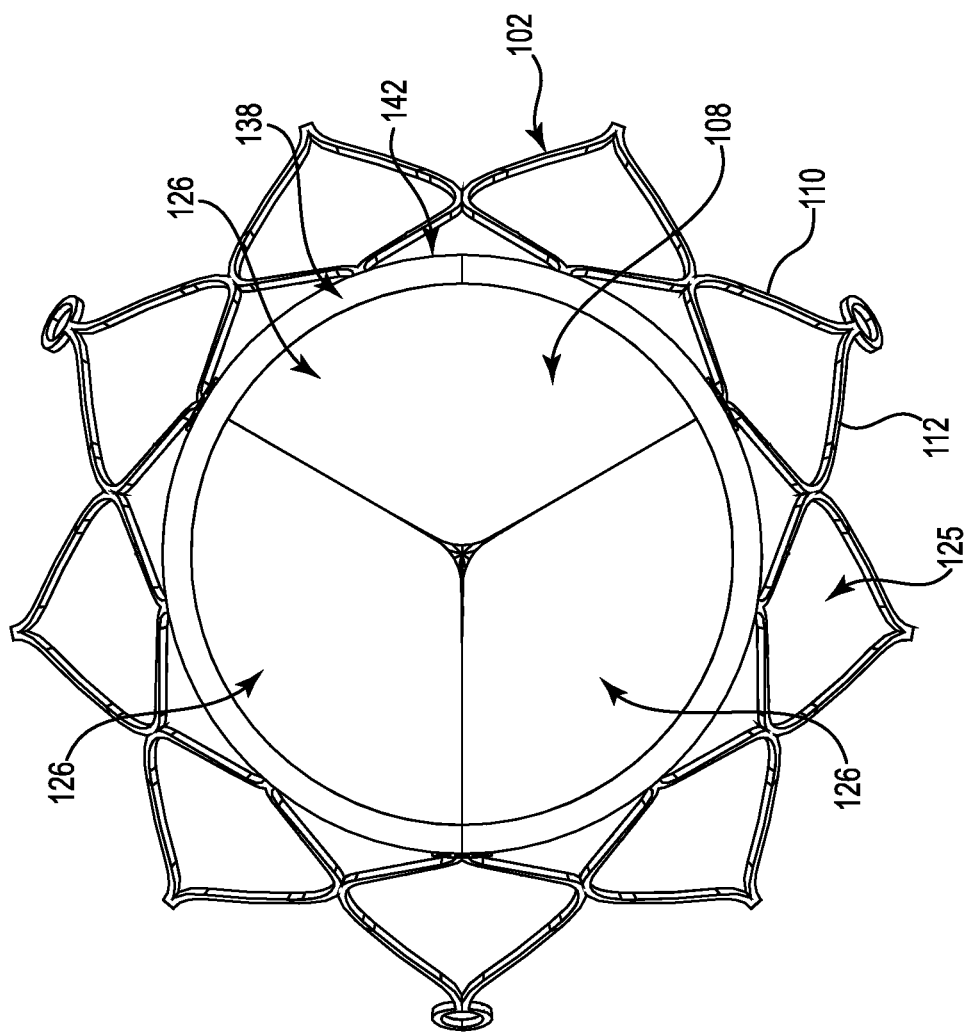
FIG. 4 is a view from a distal end of the heart valve replacement device of FIG. 1.
Figure 5:
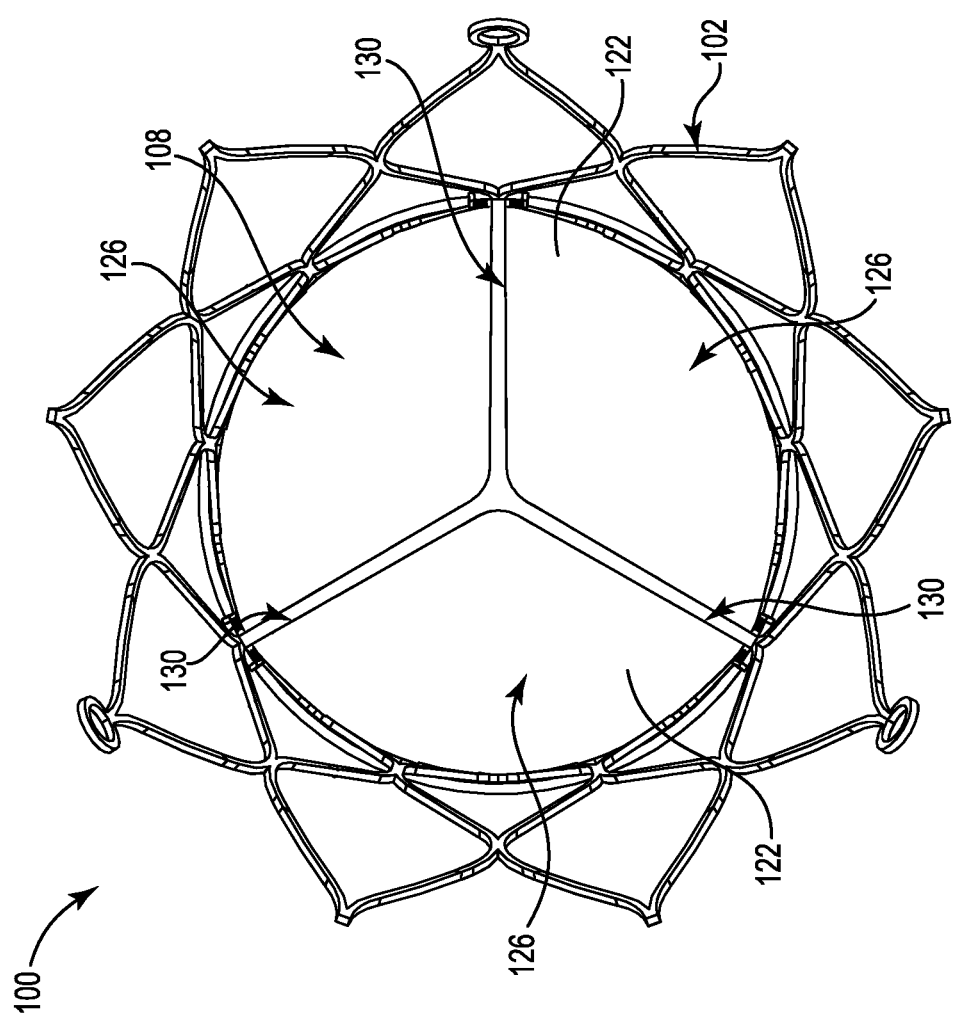
FIG. 5 is a view from a proximal end of the heart valve replacement device of FIG. 1.

The present disclosure relates to replacement heart valves for use in the mitral valve, tricuspid valve, aortic valve or pulmonary valve of the heart. In some circumstances, a replacement heart valve may be disposed within the native valve such that portions of the replacement heart valve, or portions of a device such as a stent attached to the replacement heart valve, are adjacent to the native heart valve.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

FIGS. 1-5 show one embodiment of a heart valve replacement device 100 comprising a stent 102 having a proximal end 104 and a distal end 106, and a valve 108 disposed within a lumen of the stent and connected to the stent 102 at a position distal from the proximal end 104. The stent 102 may have any configuration and may be expandable from a first position to an expanded position. As shown in FIGS. 1-5, the stent 102 is in the expanded position. The stent 102 may be self-expandable, balloon-expandable, or otherwise expandable from the first position to the second position. The stent 102 may have an outer surface 110 and an inner surface 112, where the inner surface 112 defines a lumen 114 over at least a portion of the stent. In at least one embodiment, the outer surface 110 may have a layer of a coating material. In at least one embodiment, the inner surface 112 may have a layer of a coating material to reduce friction with the valve 108. The stent 102 may have one or more attachment features 115 on the outer surface 110, inner surface 112, or both for connecting the valve 108 to the stent 102. In at least one embodiment, at least one of the attachment feature 115 may have a radiopaque markers or a coating for imaging purposes in order to assist with positioning of the heart valve replacement device 100 within the vascular system.

The valve 108 may be attached to the stent with sutures or with other mechanical means at one or more attachment features 115. The valve 108 may also be attached to the stent 102 with an adhesive. The valve 108 may be attached to the stent 102 with the adhesive at the attachment features. The valve 108 may also be attached to the stent 102 with a polymer attachment layer. The valve 108, in some embodiments, may be attached with one or more of sutures, other mechanical attachment means, adhesive, or the polymer attachment layer.

The valve 108 may be constructed, in some embodiments, from a single piece of tissue material. In some embodiments, the tissue material may be a biomaterial. In some embodiments, the tissue material may be a cross-linked collagen based-biomaterial that comprises acellular or cellular tissue selected from the group consisting of cardiovascular tissue, heart tissue, heart valve, aortic roots, aortic wall, aortic leaflets, pericardial tissue, connective tissue, dura mater, dermal tissue, vascular tissue, cartilage, pericardium, ligament, tendon, blood vessels, umbilical tissue, bone tissue, fasciae, and submucosal tissue and skin. In some embodiments, the tissue material is an implantable biomaterial such as the biomaterial described in the disclosure of U.S. Pat. No. 9,205,172, filed on Dec. 21, 2005 and entitled "Implantable Biomaterial and Method of Producing Same," which is incorporated by reference herein in its entirety. In some embodiments, the tissue material may be artificial tissue. In some embodiments, the artificial tissue may comprise a single piece molded or formed polymer. In some embodiments, the artificial tissue may comprise polytetrafluoroethylene, polyethylene terephthalate, other polymers, and other polymer coatings.

The valve 108 may have a proximal end 116 and a distal end 118. The valve 108 may have an outer surface 122 and an inner surface 124, where the inner surface 124 defines a lumen 125. The valve 108 may have at least one leaflet 126. In some embodiments, the valve 108 comprises at least three leaflets 126 that are connected to one another. In some embodiments, the valve 108 may comprise three leaflets 126. In some embodiments, the valve 108 may comprise two leaflets 126. In some embodiments, the valve 108 may comprise four leaflets 126. In some embodiments, the valve 108 may comprise more than four leaflets 126. The leaflets 126 may each form cup-like concave portions 128. Thus, the leaflets 126 are not flat pieces of tissue, but rather formed into a curved shape. Studies such as the one published in an article entitled *Flat or Curved Pericardial Aortic Valve Cusps: A Finite Element Study*, authored by Khee Hiang Lim, Johanes Candral, Joon Hock Yeo and Carlos M. G. Duran, Journal of Heart Valve, Vol. 13, No. 5 (September 2004), which is incorporated by reference herein in its entirety, have demonstrated that three-dimensional leaflet cusps similar to those shown herein have about a 35% reduction in stresses over a flat piece of tissue. The leaflets 126 are positioned adjacent to one another at commissures 130. The valve 108 may further comprise a body portion 132 connected to at least the leaflets 126. In some embodiments, the body portion 132 may be positioned distally relative to the leaflets. In at least one embodiment, the valve 108 may have an annulus region 138 at the distal end 112. The annulus region 136 may be connected to the body portion 132. In some embodiments, the valve 108 may have a cuff portion 140 attached to the annulus region 138. The cuff portion 140 may have an outer surface 142 and an inner surface 144. The cuff portion 140 may extend proximally over at least part of the body portion 132. The cuff portion 140 may, in some embodiments, be expandable to form a seal against the native tissue. In some embodiments, the valve 108 may further comprise a first edge 146 and a second edge 147 that form a seam 148 that extends axially along the valve 108. In some embodiments, the seam 148 may be joined with some adhesive or other chemical process. In some embodiments, the first edge 146 and the second edge 147 may be joined across seam 148 by one suture. In some embodiments, the first edge 146 and the second edge 147 may be joined across seam 148 by a first suture near a proximal end of the seam 148 and a second suture near a distal end of the seam 148. In some embodiments, the first edge 146 and the second edge 147 may be joined across seam 148 by a first suture near a proximal end of the seam 148, a second suture near a distal end of the seam 148, and at least one suture between the first suture and the second suture. In other embodiments, the seam 148 may form a relatively small gap between the first edge 146 and a second edge 147 without compromising performance of the valve. In some embodiments, the leaflets 126 may have a thickness between the outer surface 122 and the inner surface 124 that is less than the thickness of the body region.

The valve 108 may be disposed relative to the stent 102 such that the outer surface 122 of at least part of the valve 108 abuts the inner surface 112 of the stent 102. As shown at least in FIG. 3, the valve 108 may be attached to stent 102 with sutures 150. Sutures 150 may be used to connect the cuff portion 140 to one of the body portion 132 or the stent 102. Sutures 150 may be used to connect the body portion 133 to the stent 102. Sutures 150 may be used to connect the commissures 130 to the stent 102. In at least one embodiment, sutures 150 may be used to connect the commissures 130 to the stent 102 at an attachment point 115. In some embodiments, the outer surface 122 of at least the body portion 132 abuts the inner surface 112 of the stent 102. In some embodiments, the inner surface 144 at the cuff portion 140 abuts the outer surface 110 of the stent 102 in the first position. In some embodiments, the inner surface 144 at the cuff portion 140 abuts the outer surface 110 of the stent 102 in the second, expanded position as shown in FIGS. 1-5. In some embodiments, when deployed in the native valve and due to the fluid flow of blood in the valve or blood pressure in the vessel, the cuff portion 140 may expand or move away from the outer surface 110 of the stent 102 to form a seal against the native heart structure.

Figure 6:
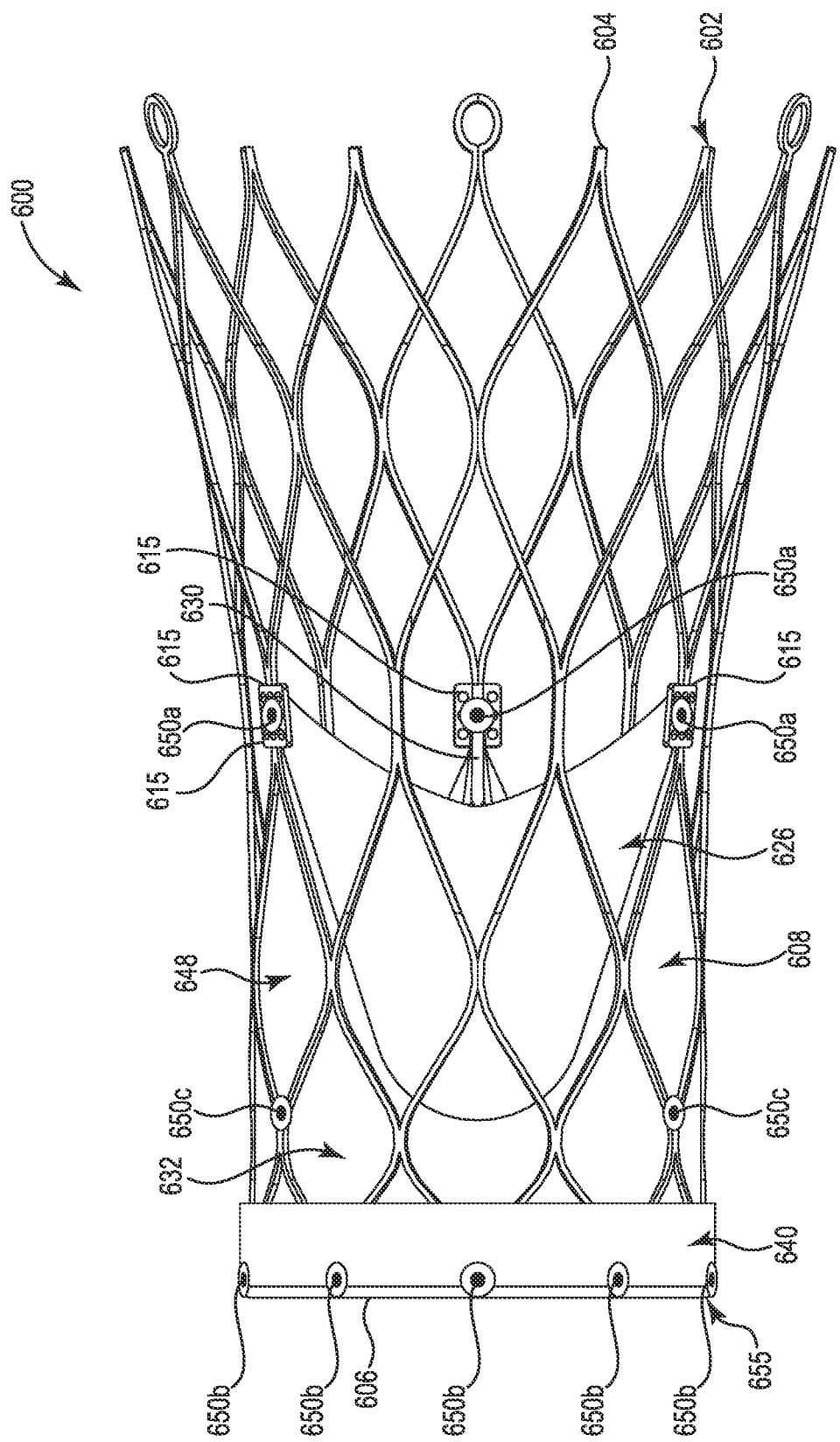
FIG. 6 is a perspective view of a heart valve replacement device comprising a heart valve disposed relative to the stent construct, in accordance with one embodiment of the present disclosure.
Figure 7:
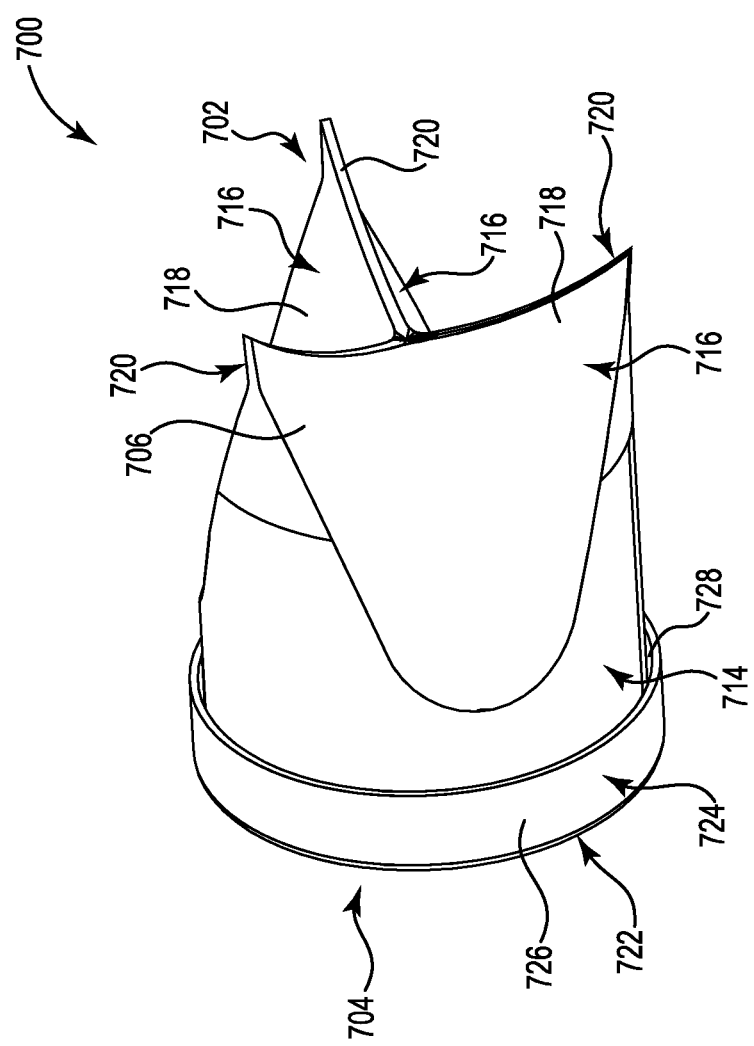
FIG. 7 is a perspective view of a heart valve, in accordance with one embodiment of the present disclosure.
Figure 8:
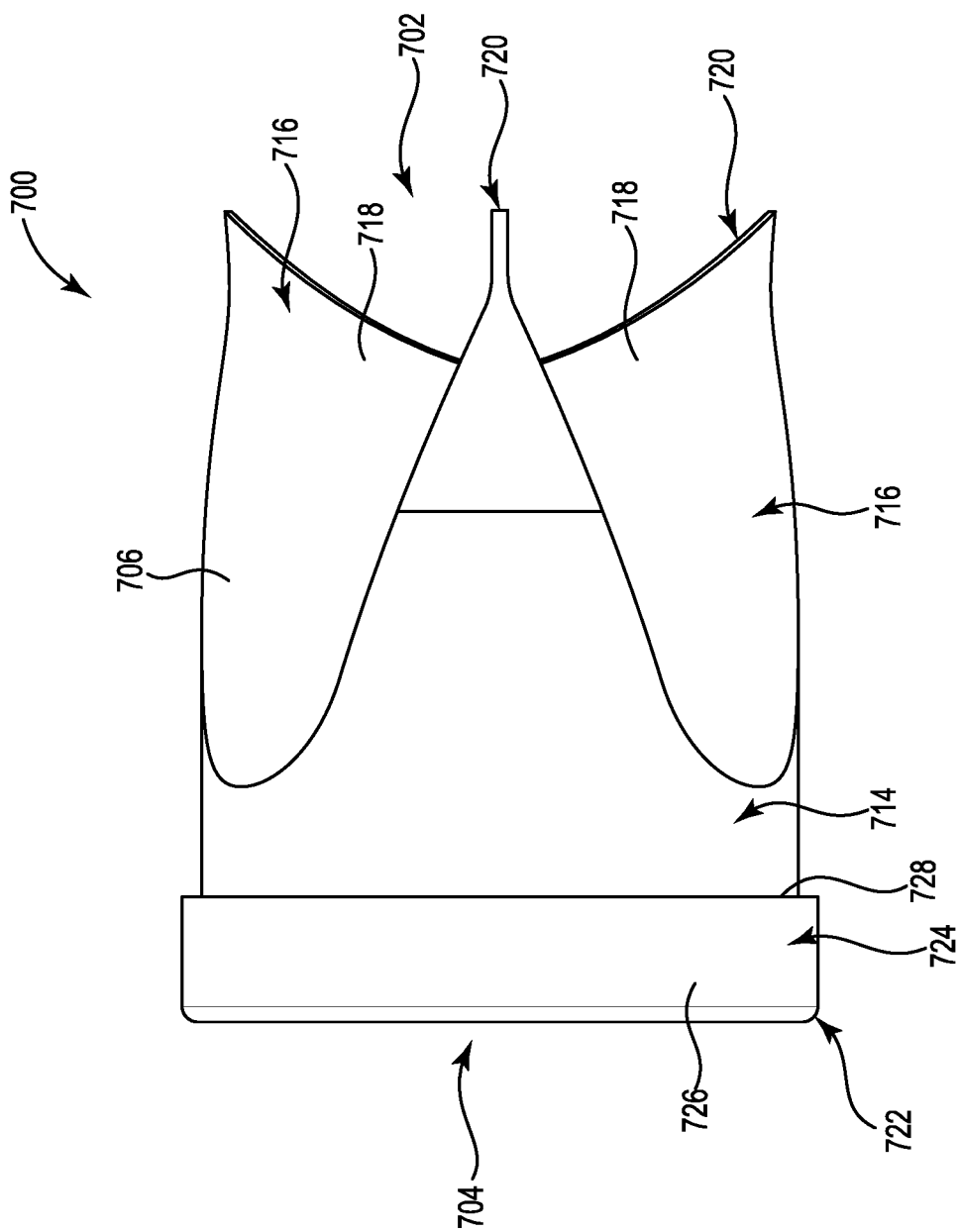
FIG. 8 is a side view of the heart valve of FIG. 7.
Figure 9:
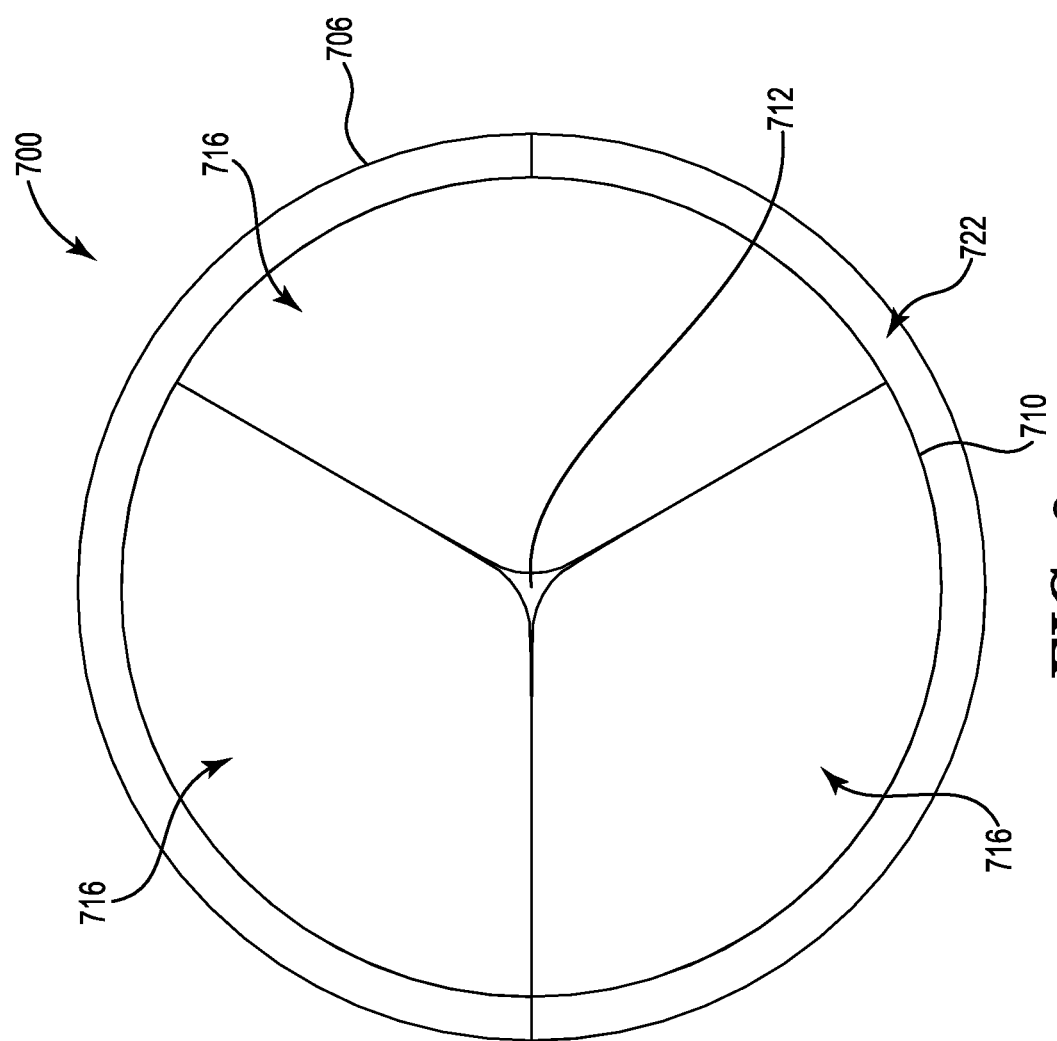
FIG. 9 is a view from a distal end of the heart valve of FIG. 7.
Figure 10:
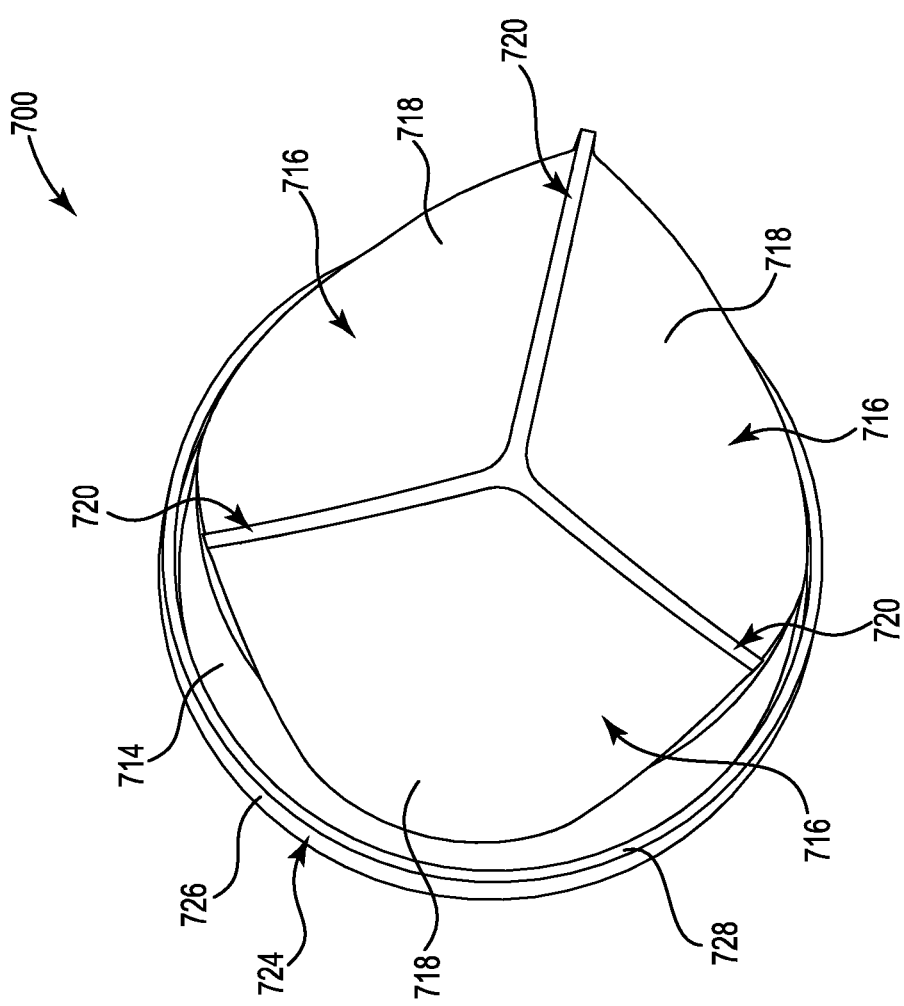
FIG. 10 is a view from a proximal end of the heart valve of FIG. 7.

At least in part because the valve is formed from a single piece of material, the valve may be attached to the stent with minimal sutures. In some embodiments, FIG. 6 shows one embodiment of the heart valve replacement device 600 with a valve 608 attached to a stent 602 with only fifteen sutures 650. The valve 608 is attached to the stent 602 at least at attachment features 615. In some embodiments, the attachment features 615 may be aligned with the commissures 630 between the leaflets 626 of the valve 608. The valve 608 may be attached with a first set of sutures 650a at the attachment features 615. In at least one embodiment, the first set of sutures 650a comprises three sutures 650. The valve 608 may further be attached with a second set of sutures 650b at or near the end of the stent. In some embodiments, the sutures of the second set of sutures 650b may join the cuff portion 640 of the valve 608 to the stent 602. In some embodiments, the sutures of the second set of sutures 650b may join the cuff portion 640 to the body portion 632 overlapped by the cuff portion 640. In at least one embodiment, the second set of sutures 650b may be a running set of sutures that traverses the circumference of the valve 608 on the outer surface 622 of the valve near the distal end of the stent. In at least one embodiment, the second set of sutures 650b may be a running set of sutures that traverses the circumference of the valve at the edge 655 at the distal end 606 of the stent 602. In at least one embodiment, the second set of sutures 650b comprises nine sutures 650. In at least one embodiment, the valve 608 may be attached with a third set of sutures 650c. The third set of sutures 650c may be positioned axially between the first set of sutures 650a and the second set of sutures 650b. The third set of sutures 650c may connect the body portion 632 to the stent 602. The third set of sutures 650c may comprise three sutures 650. The third set of sutures 650c may, in some embodiments, each be axially aligned with the first set of sutures 650a. The third set of sutures 650c may, in some embodiments, each be radially offset and distally positioned from the sutures of the first set of sutures 650a. In at least one embodiment, at least one suture of the third set of sutures 650c may connect the tissue across the seam 648 of the valve 602. Other arrangements of sutures are contemplated by this invention.

FIGS. 7-10 shows an embodiment of the valve 700, which may be formed as a cylindrical structure prior to insertion into a stent construct or other structure for deployment to the native valve, rather than as a flat sheet of tissue prior to insertions into the stent construct. In some embodiments, the tissue material may be artificial tissue. In some embodiments, the tissue material may be a biomaterial. In some embodiments, the tissue material may be a cross-linked collagen based-biomaterial that comprises acellular or cellular tissue selected from the group consisting of cardiovascular tissue, heart tissue, heart valve, aortic roots, aortic wall, aortic leaflets, pericardial tissue, connective tissue, dura mater, dermal tissue, vascular tissue, cartilage, pericardium, ligament, tendon, blood vessels, umbilical tissue, bone tissue, fasciae, and submucosal tissue and skin. In some embodiments, the tissue material is an implantable biomaterial such as the biomaterial described in the disclosure of U.S. Pat. No. 9,205,172, filed on Dec. 21, 2005 and entitled "Implantable Biomaterial and Method of Producing Same," which is incorporated by reference herein in its entirety. The valve 700 has a proximal end 702 and a distal end 704. The valve 700 may have an outer surface 706 and an inner surface 710, where the inner surface 710 defines a lumen 712. In some embodiments, the valve 700 comprises a body portion 714 and at least three leaflets 716 that are connected to the body portion 714. In some embodiments, the valve 700 may comprise three leaflets 716. In some embodiments, the valve 700 may comprise four leaflets 716. In some embodiments, the valve 700 may comprise more than four leaflets 716. The leaflets 716 may have curved portions 718. The curved portions 718 may form cup-like concave portions. The leaflets 716 are positioned adjacent to one another at commissures 720. In at least one embodiment, the valve 108, the body portion 714 may have an annulus region 722 at the distal end 704. In some embodiments, the valve 700 may have a cuff portion 724 attached to the annulus region 722. The cuff portion 724 may have an outer surface 726 and an inner surface 728. The cuff portion 724 may extend proximally over at least part of the body portion 714. The cuff portion 724 may, in some embodiments, be expandable to form a seal against the native tissue.

Figure 11:
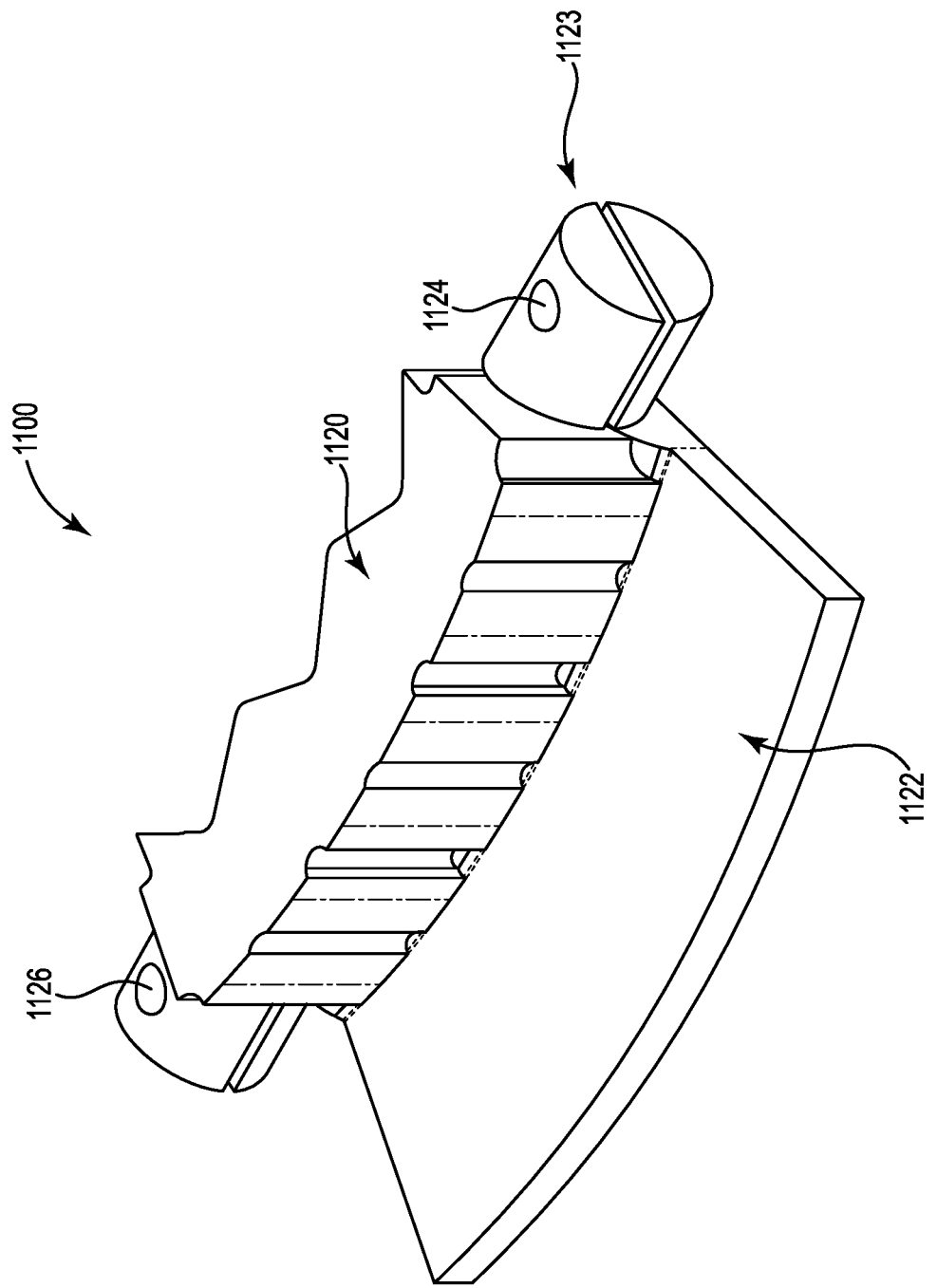
FIG. 11 is a perspective view of a mold assembly for fabricating a heart valve of the present disclosure having a first mold portion and a second mold portion, in accordance with one embodiment of the present disclosure.

In some embodiments, a method for manufacturing a valve of the present disclosure may comprise inserting a sheet of tissue into a mold in order to form the leaflets and the cuff, and then, in some embodiments, forming the molded tissue into a circular ring. FIGS. 11-14 show one embodiment of a mold 1100. The mold may comprise an upper portion 1120 and a lower portion 1122. The upper portion 1120 and the lower portion 1122 may be separate components or may be connected to one another. In at least one embodiment, the upper portion 1120 and the lower portion 1122 may be formed as a clamshell-like structure such that the upper portion 1120 and the lower portion 1122 are pivotably connected to one another at least at one hinge point. FIG. 11 shows the mold in a closed position. In at least one embodiment, the upper portion 1120 and the lower portion 1122 may be fixedly joined to one another in the closed position with a locking means 1123. In one embodiment, the locking means 1123 may comprise a first hole 1124 in the upper portion 1120 and a second hole 1126 in the upper portion 1120, as well as a first hole 1128 in the lower portion 1122 and a second hole 1130 in the lower portion 1122 that are capable of aligning with the first hole 1124 and the second hole 1126. Bolts can be inserted into the first holes 1124, 1128 and the second holes 1128, 1138 and tightened with a nut. The locking means 1123 may also comprise clamps that push the upper portion 1120 and the lower portion 1122 together. Other means for locking the upper portion 1120 into a position relative to the lower portion 1122 in a closed position is contemplated by this invention. When the locking means 1123 is engaged, a desired pressure may be applied to any tissue positioned within the mold.

Figure 12:
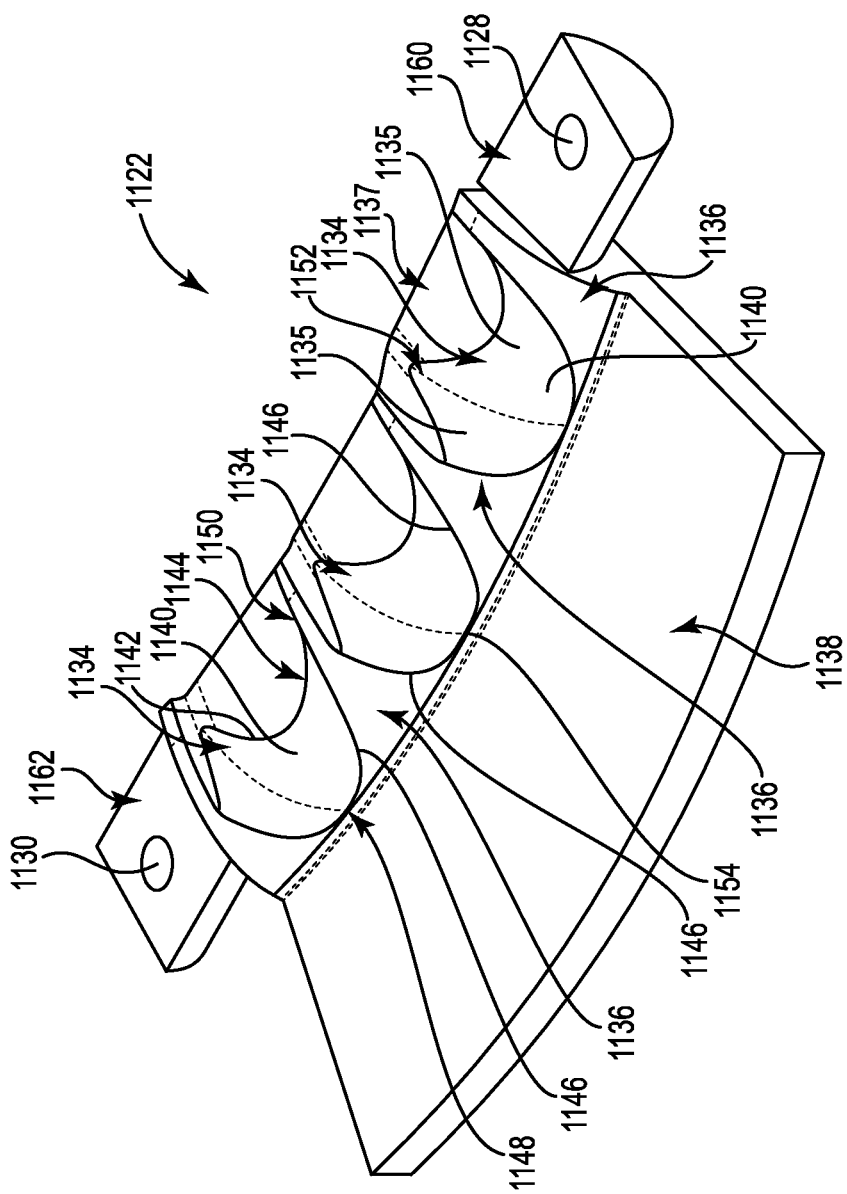
FIG. 12 is a top view of the first mold portion of the mold assembly of FIG. 11.

The lower portion 1122 of the mold 1100 is shown in FIG. 12. The lower portion 1122 comprises at least one leaflet region 1134, a commissure region 1136 between adjacent leaflet regions 1134, and a body region 1138 connected to the commissure regions 1136 and leaflet regions 1134. As shown in FIG. 12, the lower portion 1122 has three leaflet regions 1134. In some embodiments, the lower portion 1122 may have two leaflet regions 1174. In some embodiments, the lower portion 1122 may have four leaflet regions 1134. In some embodiments, the lower portion 1122 may have more than four leaflet regions 1134. In at least one embodiment, the leaflet region 1134 may comprise male forming features. The leaflet region 1134 may comprise at least one convex forming section 1135 and a recessed region 1137. The at least one convex forming section 1135 may have a curvilinear outer surface 1140, a first curvilinear edge 1142 at a first end 1144, and a second curvilinear edge 1146 bordering the adjacent commissure region 1136 and extending from the first end 1144 to a second end 1148. The first curvilinear edge 1142 may form a parabola. The first curvilinear edge 1142 and the second curvilinear edge 1146 may intersect at a point 1150. As shown in FIG. 12, the leaflet region 1134 has two convex forming sections 1135. The first curvilinear edge 1142 of the first convex forming section intersects the first curvilinear edge 1142 of the second convex forming section at a point 1152. The point 1152 may be positioned above the recessed region 1137. The first curvilinear edges 1142 each form a parabola. The second curvilinear edge 1146 of the first convex forming section 1135 intersects the second curvilinear edge 1146 of the second convex forming section 1135 at a point 1144. The second curvilinear edge 1146 of the first convex forming section 1135 and the second curvilinear edge 1146 of the second convex forming section 1135 may form a parabola. In some embodiments, the shape of the leaflet region 1134 may be similar to the leaflet templates as described in the disclosure of U.S. Pat. No. 6,491,511, filed on Oct. 14, 1999 and entitled "Mold to Form Stent-Less Replacement Heart Valves from Biological Membranes," which is incorporated herein by reference. The body region 1138 may be connected to the commissure regions 1136. The body region 1138 may be substantially flat and extend outward from the lower portion 1122. In some embodiments, the lower portion 1122 has locking flanges 1160, 1162 extending outwardly on either side of the leaflet regions 1134 with the first hole 1128 and second hole 1130 in each respective locking flange 1160, 1162.

Figure 13:
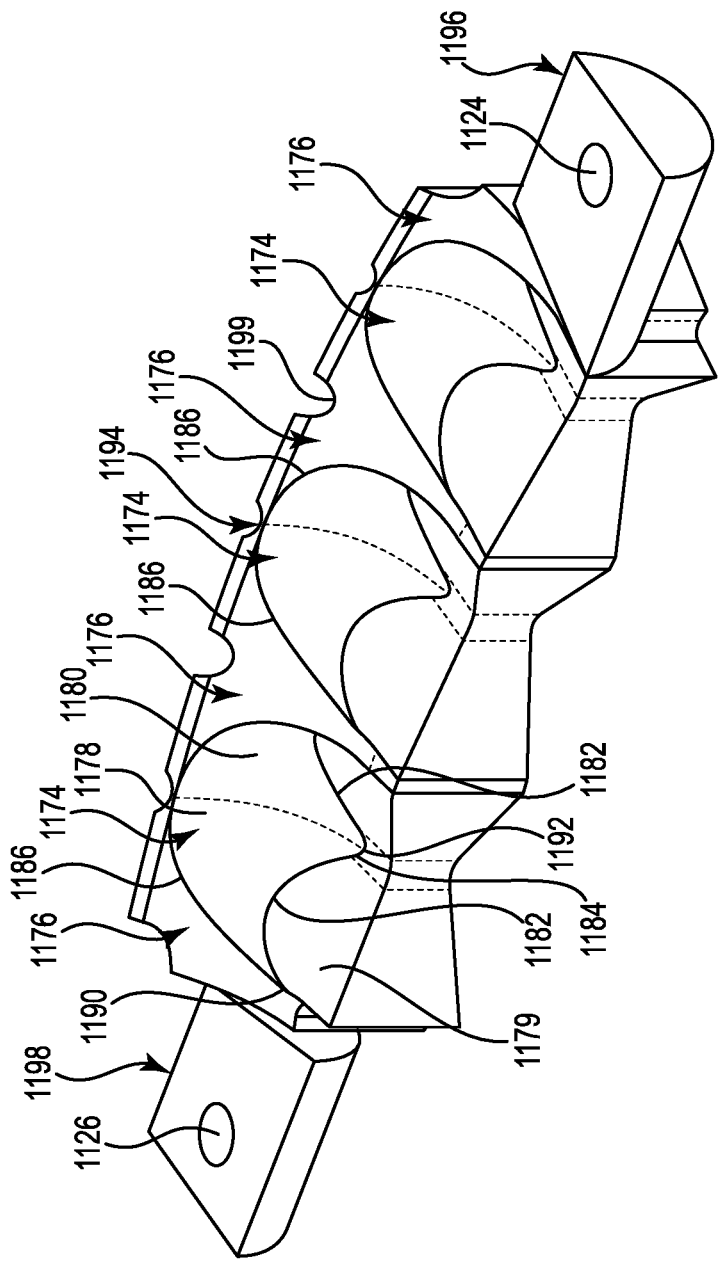
FIG. 13 is a bottom view of the second mold portion of the mold assembly of FIG. 11.
Figure 14:
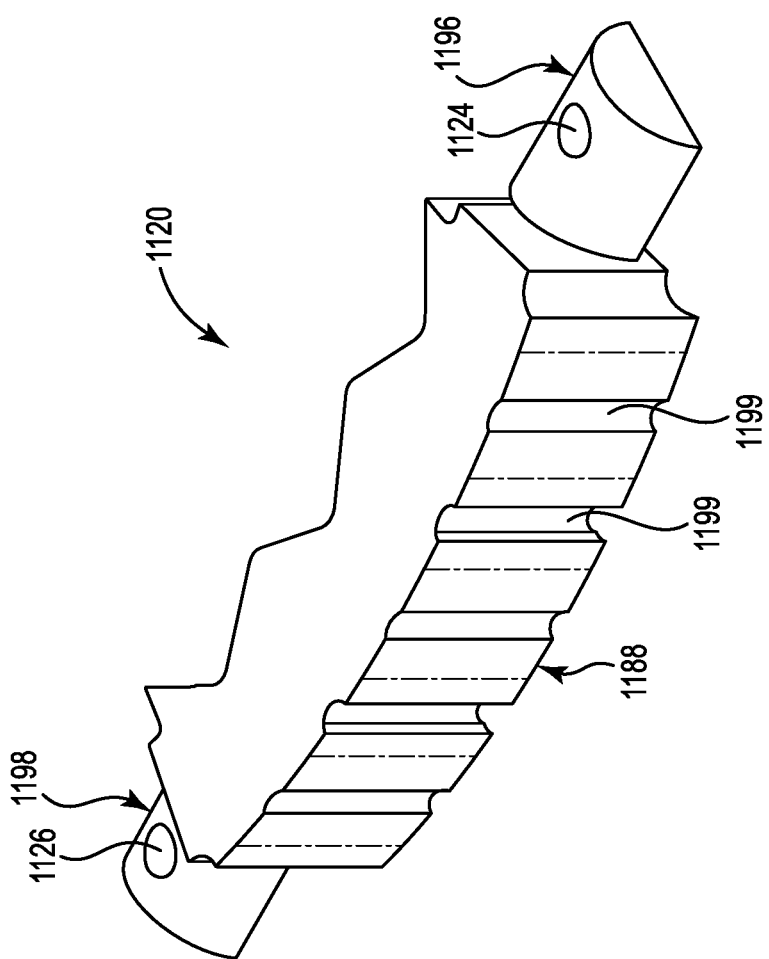
FIG. 14 is a top view of the second mold portion of FIG. 11.

The upper portion 1120 of the mold 1100 is shown in FIGS. 13-14. The upper portion 1120 comprises at least one leaflet region 1174 and a commissure region 1176 between adjacent leaflet regions 1174. As shown in FIG. 13, the upper portion has three leaflet regions 1174. In some embodiments, the upper portion 1120 may have two leaflet regions 1174. In some embodiments, the upper portion 1120 may have four leaflet regions 1174. In some embodiments, the upper portion 1120 may have more than four leaflet regions 1174, In at least one embodiment, the leaflet region 1174 may have female forming features that mate with corresponding male forming features on the leaflet region 1134 of the lower portion 1122. The leaflet region 1174 may, comprise at least one concave forming section 1178 and a second section 1179. When in the closed position, the at least one concave forming section 1178 of the upper portion 1120 mates with the at least one convex forming section 1136 of the lower portion 1122. The at least one concave forming section 1178 may have a curvilinear surface 1180, a first curvilinear edge 1182 at a first end 1184, and a second curvilinear edge 1186 bordering the adjacent commissure region 1176 and extending from the first end 1184 to a second end 1188. In some embodiments, the second end 1148 of the lower portion 1148 is aligned with the second end 1188 of the upper portion, when the mold is in the closed position. The first curvilinear edge 1182 may form a parabola. The first curvilinear edge 1182 and the second curvilinear edge 1186 may intersect at a point 1190. The first curvilinear edge 1182 of the first concave forming section intersects the first curvilinear edge 1182 of the second concave forming section at a point 1192. The point 1192 may be positioned adjacent the second section 1179. The first curvilinear edges 1182 each form a parabola. The second curvilinear edge 1186 of the first concave forming section intersects the second curvilinear edge 1186 of the second concave forming section at a point 1194. The second curvilinear edge 1186 of the first concave forming section and the second curvilinear edge 1186 of the second concave forming section may form a parabola. In some embodiments, the shape of the leaflet region 1174 may be similar to the leaflet templates as described in the disclosure of U.S. Pat. No. 6,491,511, filed on Oct. 14, 1999 and entitled "Mold to Form Stent-Less Replacement Heart Valves from Biological Membranes," which is incorporated herein by reference. In some other embodiments, a body region may be connected to the commissure regions 1176 and leaflet regions 1174. The body region may be connected to the commissure regions 1176. The body region 1138 may be substantially flat and extend outwardly from the commissure regions 1176. The body region may overlap at least a portion the body region of the lower portion 1122 when in the closed position. The body region of the upper portion 1120 may be relatively shorter than the body region of the lower portion. The edge of the body region of the upper portion 1120 may determine the edge of the annulus region of the resulting valve. In some embodiments, the upper portion 1120 has locking flanges 1196, 1198 extending outwardly on either side of the leaflet regions 1174 with the first hole 1124 and second hole 1126 in each respective locking flange 1196, 1198. Upper portion 1120 may also have a number of channels 1199 near the second end 1188.

In some embodiments, the mold may be formed from a metal, a polymer or a ceramic material. In some embodiments, the mold may be printed using additive manufacturing such that the mold could be individually created for a patient and form a valve specific to that patient.

In at least one embodiment, a sheet of tissue may be inserted into the mold 1100 between the lower portion 1122 and the upper portion 1124. The locking means 1123 may then be engaged so that the lower portion 1122 and the upper portion 1124 are fixed in a closed position. In at least one embodiment, where the sheet of tissue is formed from a biomaterial, a cross-linking solution glutaraldehyde may be applied to the sheet of tissue in order to facilitate cross-linking of the tissue. In some embodiments, the cross-linking solution comprises glutaraldehyde. In some embodiments, the cross-linking solution may be injected into the tissue, and in other embodiments the tissue may be soaked, immersed in, or penetrated with the cross-linking solution. In some embodiments, the glutaraldehyde may be injected into the tissue, and in other embodiments the tissue may be soaked, immersed in, or penetrated with glutaraldehyde. In at least one embodiment, the mold 1100 with the sheet of tissue inserted into the mold, may be immersed into the cross-linking solution, which may comprise glutaraldehyde. In at least one embodiment, the upper portion 1124 may be removed from the mold 1100 when the tissue is partially cross-linked and the tissue may be removed from the mold 1100 once it is fully cross-linked. In at least one embodiment, the upper portion 1124 is removed from the mold 1100 while the mold 1100 remains immersed in the cross-linking solution or glutaraldehyde. In at least one embodiment, a spacer or a spacing layer may be inserted between one of the lower portion 1122 and the upper portion 1124 before the glutaraldehyde is applied to the sheet of tissue.

Figure 15:
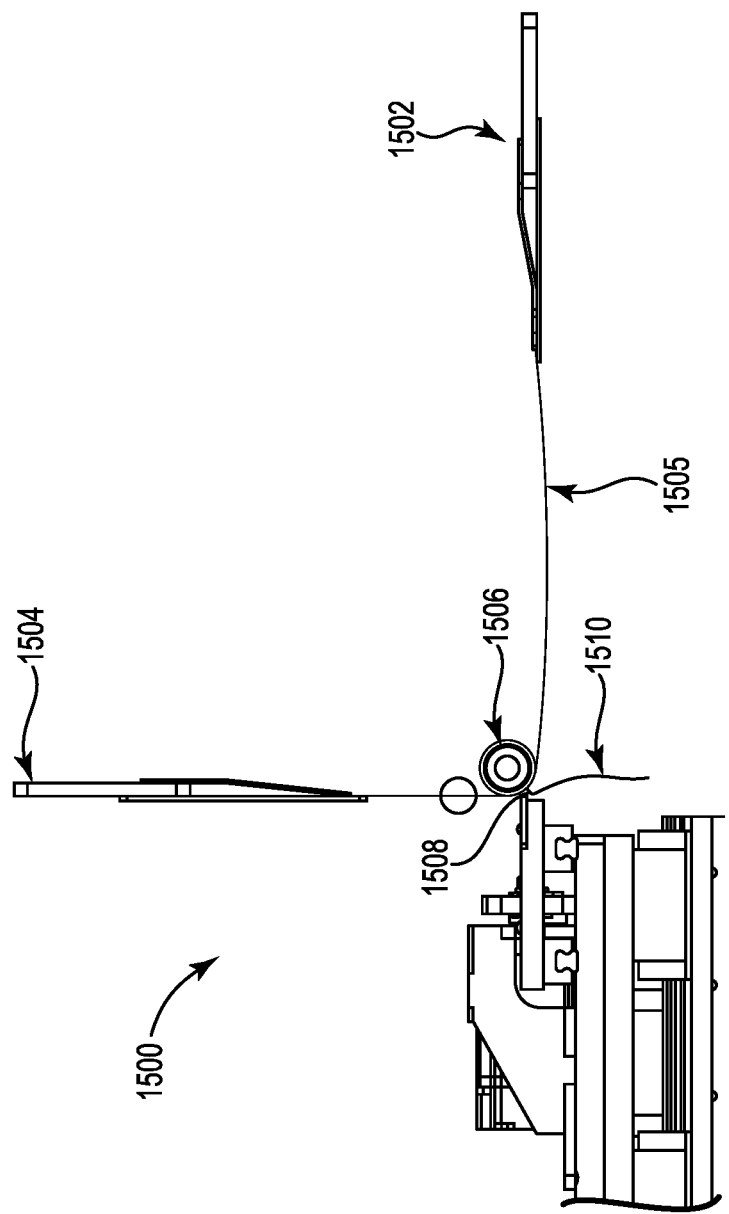
FIG. 15 is a schematic of a cutting assembly for fabricating the heart valve from the biomaterial, in accordance with one embodiment of the present disclosure.

In some embodiments, the valve may be constructed from a single sheet of material having varying thickness. In some embodiments, a method for manufacturing a sheet of tissue for the valve may comprise using a cutting system 1500 as shown in FIG. 15. Cutting system 1500 may have a first tissue holder 1502 and a second tissue holder 1504 that apply tension to the sheet of tissue 1505 held by and between the two tissue holders 1502, 1504. In at least one embodiment, one of the first tissue holder 1502 and the second tissue holder 1504 may be driven by a servo motor to move the tissue in a first direction. In at least one embodiment, each of the first tissue holder 1502 and the second tissue holder 1504 are driven by a servo motor. In such an embodiment, the servo motor of the first tissue holder 1502 moves in synchrony with the servo motor of the second tissue to maintain a predetermined, constant tension in the sheet of tissue 1505. In at least one embodiment the second tissue holder 1504 may be positioned perpendicular to the first tissue holder 1502. A roller 1506 may be positioned between the first tissue holder 1502 and the second tissue holder 1504. In some embodiments, the cutting system 1500 may have roller 1506 is driven by a motor that moves the tissue from the first tissue holder to the second tissue holder. The roller 1506 may be aligned with both the first tissue holder 1502 in a first direction and the second tissue holder 1504 in a second direction. In at least one embodiment, the roller 1506 positions the tissue in relation to a cutting blade 1508. The cutting system 1500 may have blade 1508 that is operably connected to a motor-driven shaft that is capable of controllably moving the blade towards the roller 1506 (and thus towards the tissue) or away therefrom depending on a desired thickness of the tissue. In at least one embodiment, the blade 1508 is connected to a servo motor that drives a ball screw in order to maintain precise distance accuracy. An operator, or computer instructions, may direct the user to move the blade towards or away from the tissue, resulting in a desired and variable thickness of the tissue along a sheet. In at least one embodiment, the blade is an oscillating blade, which may oscillate at a high frequency such as a frequency as high as 3,500 cycles per minute. As the tissue moves past the blade 1508, in some embodiments, the undesired tissue 1510 falls away from the remaining tissue connected to the second tissue holder 1504, essentially splitting the tissue into two parts. The desired tissue that remains connected to the tissue holders 1502, 1504 may then be cut into a sheet for insertion into a mold to then form the valve. In other embodiments, As the tissue moves past the blade 1508, the desired tissue 1510 to be used to form the valve falls away from the remaining tissue connected to the second tissue holder 1504.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

Upon reading this disclosure, those skilled in the art will appreciate still additional alternative structural and functional designs for the devices described herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention. Any feature of any embodiment described herein may be used in any embodiment and with any features of any other embodiment.

What is claimed is:

1. A heart valve replacement device comprising:
    a stent having a first end, a second end, an outer surface, and an inner surface, the inner surface defining a lumen; and
    a single-piece valve disposed within the lumen of the stent and attached to the stent, the single-piece valve being a unitary structure formed from a single sheet of a cross-linked, acellular, collagen-based biomaterial, the single-piece valve having an outer surface, an inner surface defining a lumen, and a thickness between the outer surface and the inner surface, the single-piece valve having a valve proximal end and a valve distal end, the single-piece valve consisting of:
        three molded leaflets at the valve proximal end, the three molded leaflets formed from the biomaterial, each molded leaflet having a portion formed into a curved three-dimensional shape with a concave profile, each leaflet having a thickness;
        molded commissures formed between adjacent molded leaflets, the molded commissures formed from the biomaterial; and
        a body portion, the body portion formed from the biomaterial, the body portion extending distally from the molded leaflets and from the molded commissures to the valve distal end, the body portion having a thickness, wherein the body portion, the molded commissures, and the molded leaflets are integrally formed from the single sheet of the biomaterial.

2. The heart valve replacement device of claim 1, wherein the thickness of the body portion is different than the thickness of the molded leaflets.

3. The heart valve replacement device of claim 1, wherein the body portion of the single-piece valve forms a cuff at the valve distal end.

4. The heart valve replacement device of claim 3, wherein the cuff is expandable from a first position to a second position relative to the stent.

5. The heart valve replacement device of claim 1, wherein the stent has at least one attachment feature.

6. The heart valve replacement device of claim 5, wherein at least one suture attaches the stent to the single-piece valve at one attachment feature.

7. A heart valve replacement device comprising:
    a stent having a first end, a second end, an outer surface, and an inner surface, the inner surface defining a lumen; and
    a single-piece valve disposed within the lumen of the stent and attached to the stent, the single-piece valve being a unitary structure formed from a single sheet of a cross-linked, acellular, collagen-based biomaterial, the single-piece valve having an outer surface, an inner surface defining a lumen, and a thickness between the outer surface and the inner surface, the single-piece valve having a valve proximal end, a valve distal end, a first edge extending from the proximal end to the distal end, and a second edge, opposite the first edge, extending from the valve proximal end to the valve distal end, the single-piece valve consisting of:
        three molded leaflets at the valve proximal end, the three molded leaflets formed from the biomaterial, each molded leaflet having a portion formed into a curved three-dimensional shape with a concave profile, each leaflet having a thickness;
        molded commissures formed between adjacent molded leaflets, the commissures formed from the biomaterial; and
        a body portion the body portion extending distally from the molded leaflets and from the molded commissures to the valve distal end, the body portion having a thickness, wherein the body portion, the molded commissures, and the molded leaflets are integrally formed from the single sheet of the biomaterial.

8. The heart valve replacement device of claim 7, wherein the first edge and the second edge form a seam that extends axially from the valve proximal end to the valve distal end.

* * * * *